United States Patent
Govyadinov et al.

(10) Patent No.: US 8,419,159 B2
(45) Date of Patent: Apr. 16, 2013

(54) DROP DETECTION

(75) Inventors: Alexander Govyadinov, Corvallis, OR (US); James W. Ring, Blodgett, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 732 days.

(21) Appl. No.: 12/511,639

(22) Filed: Jul. 29, 2009

(65) Prior Publication Data

US 2011/0026025 A1 Feb. 3, 2011

Related U.S. Application Data

(63) Continuation-in-part of application No. 12/388,805, filed on Feb. 19, 2009, and a continuation-in-part of application No. 12/254,864, filed on Oct. 21, 2008, now Pat. No. 7,918,528, and a continuation-in-part of application No. 12/079,338, filed on Mar. 25, 2008.

(51) Int. Cl.
*B41J 29/393* (2006.01)
*B41J 2/015* (2006.01)
*B41J 29/38* (2006.01)

(52) U.S. Cl.
USPC .................................. 347/19; 347/9; 347/20

(58) Field of Classification Search .................... 347/40, 347/19–20, 9, 44, 47
See application file for complete search history.

(56) References Cited

U.S. PATENT DOCUMENTS

| | | | |
|---|---|---|---|
| 5,621,524 A | 4/1997 | Mitani | |
| 6,648,444 B2 | 11/2003 | Valero et al. | |
| 6,814,422 B2 | 11/2004 | Bruch et al. | |
| 6,884,993 B2 | 4/2005 | Ahten et al. | |
| 7,942,494 B2 * | 5/2011 | Hayashi et al. | 347/19 |
| 8,201,913 B2 * | 6/2012 | Govyadinov et al. | 347/19 |
| 2005/0151767 A1 * | 7/2005 | Yeh et al. | 347/9 |
| 2007/0064041 A1 | 3/2007 | Sugahara | |
| 2008/0192075 A1 * | 8/2008 | Campion et al. | 347/6 |
| 2009/0091595 A1 | 4/2009 | Hayashi et al. | |
| 2009/0244141 A1 * | 10/2009 | Govyadinov et al. | 347/13 |
| 2009/0244163 A1 * | 10/2009 | Govyadinov | 347/19 |

* cited by examiner

*Primary Examiner* — Jason Uhlenhake
(74) *Attorney, Agent, or Firm* — Steven R. Ormiston

(57) ABSTRACT

In one embodiment, a drop detector includes a light source for illuminating drops passing through a drop zone and a light detector near the light source for detecting light scattered off the drops back toward the light source. In another embodiment, a drop detector includes a light source operable to emit a beam of light for illuminating drops passing through a drop zone and a light detector positioned near the light source to detect substantially only light scattered off the drops at a scatter angle θ in the range of 177° to 180°, where θ represents a direction of scattered light measured with respect to an axis of the light beam with θ=0° lying along the axis in a direction of travel of the light beam and θ=180° lying along the axis opposite the direction of travel of the light beam.

17 Claims, 6 Drawing Sheets

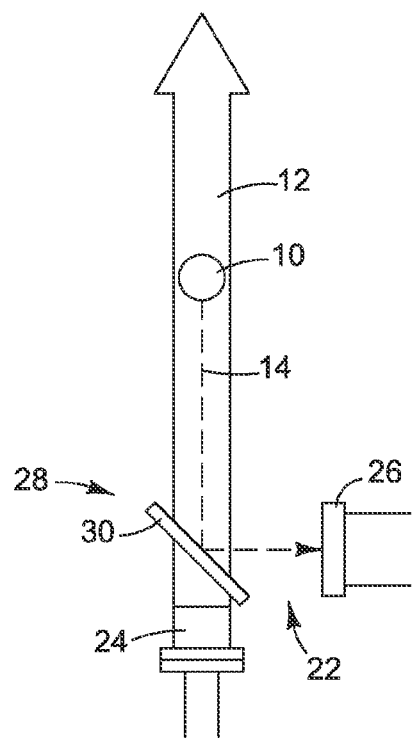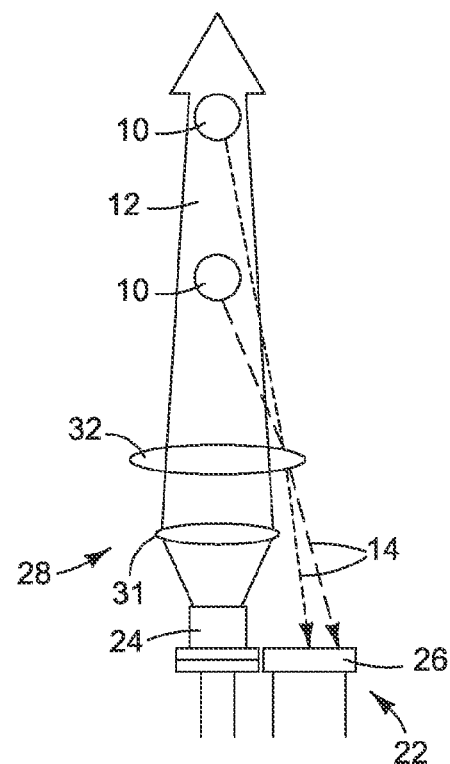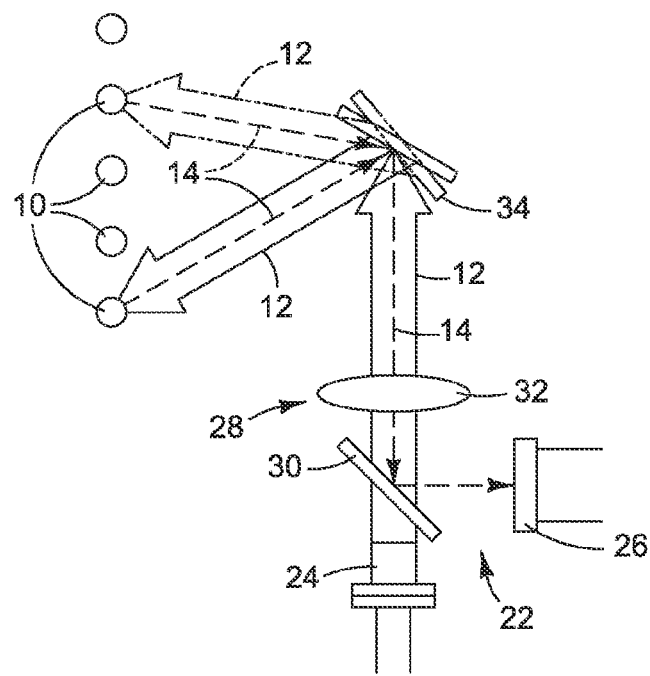

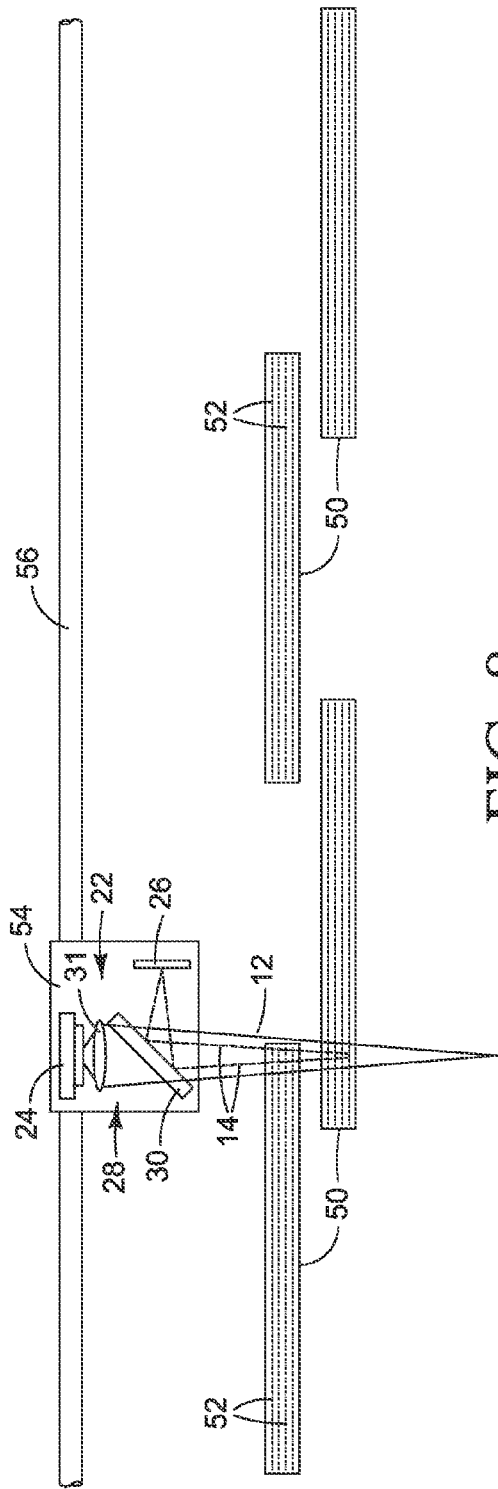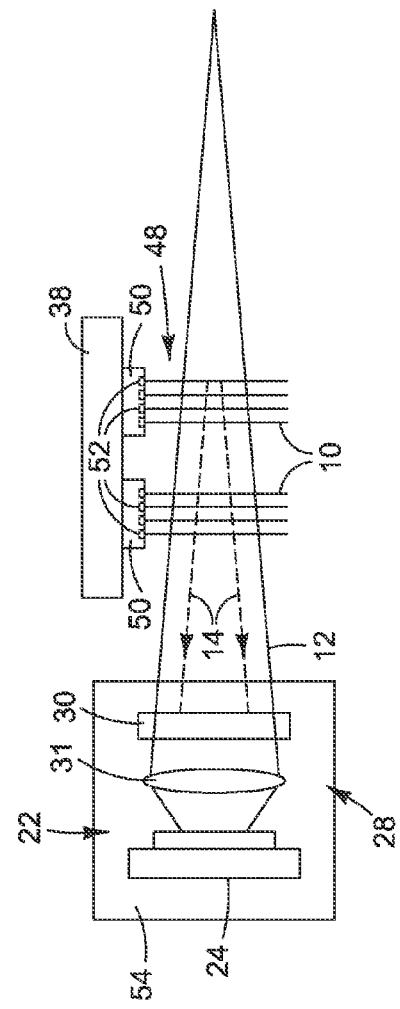

DROP DETECTION

CROSS REFERENCE TO RELATED APPLICATIONS

This application is a continuation in part and claims priority from of the following co-pending U.S. patent applications: Ser. No. 12/388,805 filed Feb. 19, 2009 titled Light Scattering Drop Detector; Ser. No. 12/254,864 filed Oct. 21, 2008 now U.S. Pat. No. 7,918,528 titled Drop Detector System And Method With Light Collector; and Ser. No. 12/079,338 filed Mar. 25, 2008 titled A Drop Detection Mechanism And A Method Of Use Thereof. This application is also related to U.S. patent application Ser. No. 12/511,583 filed contemporaneously herewith titled Drop Detection and incorporated herein by reference in its entirety.

BACKGROUND

It is sometimes desirable to detect characteristics of ink drops ejected by an inkjet printer. Characteristics of the ink drops may be used to assess the state or "health" of structural and operational features of the printer. For example, detecting that ink drops are absent where they should be present and detecting the number, size and/or shape of ink drops may help determine whether orifices through which ink drops are ejected are partially or fully clogged.

BRIEF DESCRIPTION OF THE DRAWINGS

FIGS. 4-6 illustrate various embodiments of a drop detector utilizing complete and near complete light back scatter.

FIGS. 8 and 9 are plan and end elevation views, respectively, illustrating one embodiment of a carriage mounted, movable drop detector such as might be used in the printer shown in FIG. 7.

The figures are not to scale. For example, the relative size of some features is greatly exaggerated to more clearly illustrate aspects of the various embodiments. The same part numbers designate the same or similar parts throughout the figures.

DESCRIPTION

Hewlett Packard Company is developing light scattering drop detectors (LSDD) for drop detection in inkjet printers and other drop dispensing devices. The inventors have demonstrated that it is feasible to detect and characterize drops from light scattered off the drops back toward the light source within typical inkjet printing geometries, including geometries comparable to those of a page wide array (PWA) printer drop zone. More specifically, the inventors have discovered that such "back scattered" light is more intense within a narrow band of scatter angles straight back toward the light source and that this increased intensity may be used to advantage in LSDD for PWA and other inkjet printing environments. Some embodiments are described with reference to a page wide array inkjet printer. Embodiments of the disclosure, however, are not limited to PWA inkjet printing but may be used in other printing or drop dispensing environments. The following description, therefore, should not be construed to limit the scope of the disclosure, which is defined in the claims that follow the description.

Figure 1:
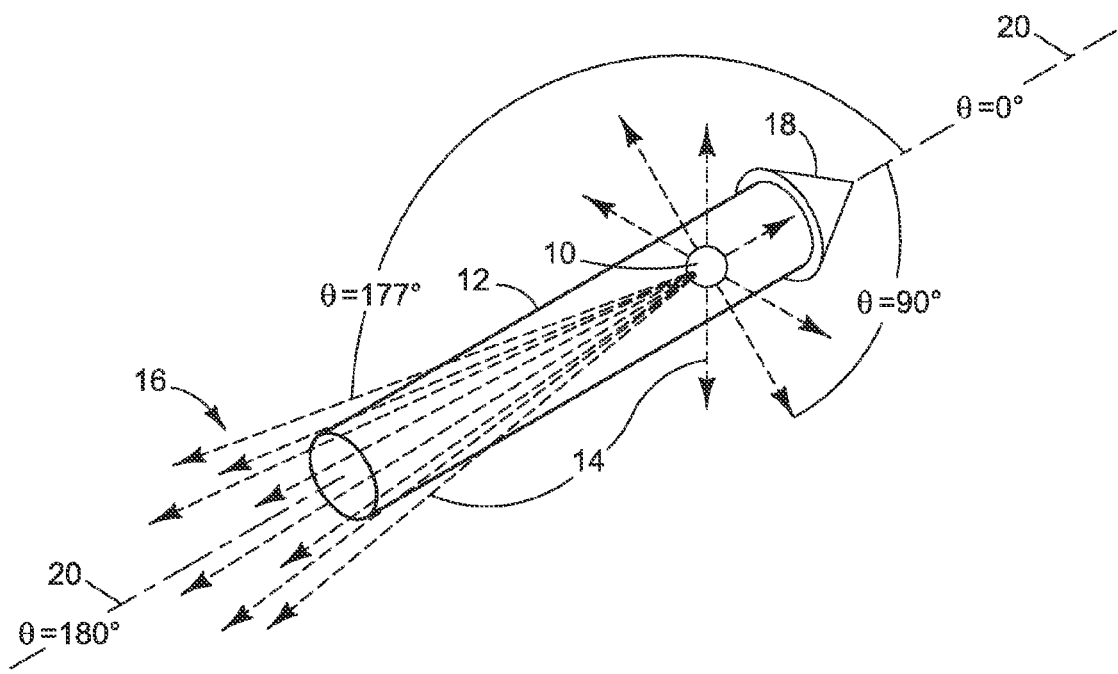
FIG. 1 illustrates one embodiment of a drop illuminated with a beam of light and a cone of light scattered back off the drop.

FIG. 1 illustrates one embodiment of a drop 10 illuminated with a beam of light 12. Dashed lines 14 indicate light from beam 12 scattered off drop 10. Light is scattered off drop 10 in all directions as represented generally by scatter lines 14. A cone of light 16 is scattered back off drop 10 at a scatter angle θ in the range of 177° to 180°. A more dense array of scatter lines 14 is included for scatter angles in the range of 177° to 180° to help depict scatter cone 16. An arrowhead 18 on light beam 12 illustrates the direction of travel of light beam 12 from a light source (not shown) toward drop 10. Scatter angle θ represents the direction of a scattered ray or rays of light measured with respect to the axis 20 of light beam 12, with θ=0° lying along axis 20 in the direction of travel of light beam 12 and θ=180° lying along axis 20 opposite the direction of travel of light beam 12. Scatter angles θ of 0° (e.g., forward scatter), 90° (e.g., side scatter) and 177° and 180° (e.g., back scatter) are specifically called out in FIG. 1 as examples to help illustrate scatter angle θ in general. As noted above, the drawings are not to scale. Thus, for example, scatter angle θ=177° is exaggerated in FIG. 1 to better illustrate scatter cone 16. Although light beam 12 is cylindrical in the embodiment shown in FIG. 1, other light beam shapes could be used.

Figure 2:
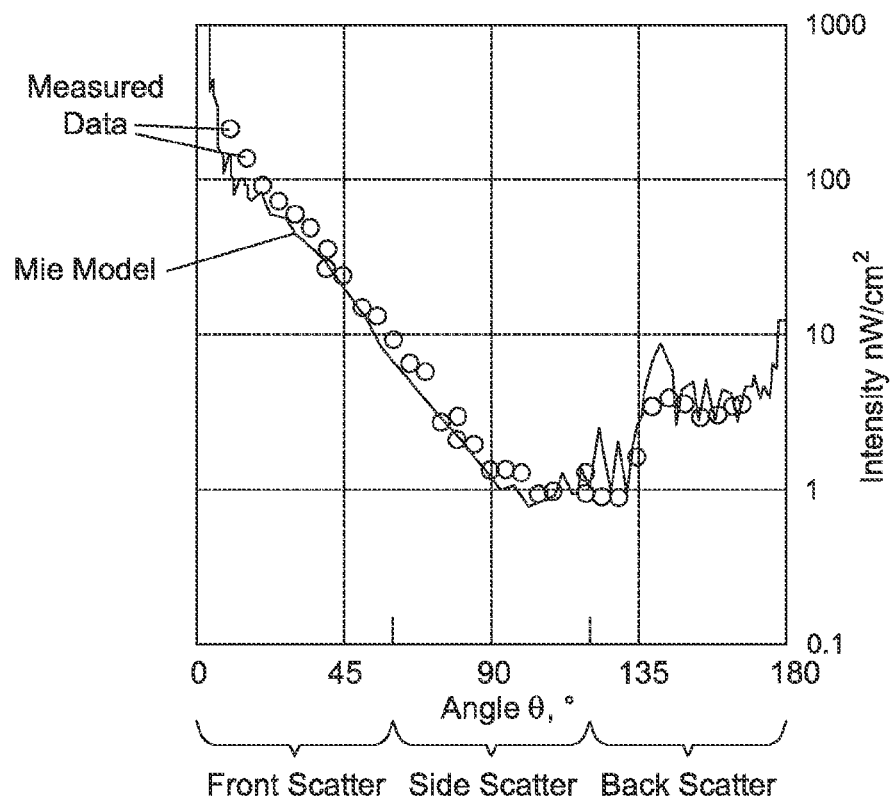
FIG. 2 is a graph illustrating the intensity of light scattered off a drop as a function of the angle of scatter.
Figure 3:
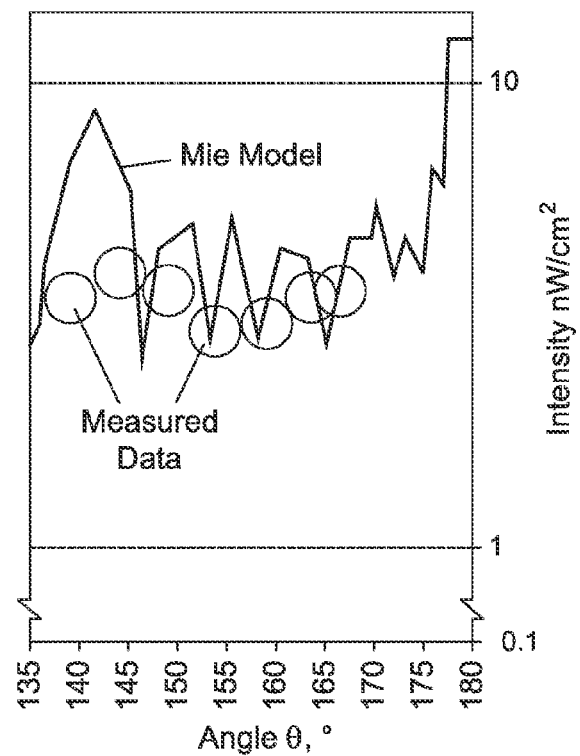
FIG. 3 is a detail view of that portion of the graph of FIG. 2 for scatter angles in the range of 135° to 180°.

FIG. 2 is a graph illustrating the intensity of light scattered off a drop as a function of the scatter angle θ. FIG. 3 is a detail view of that portion of the graph of FIG. 2 for scatter angles θ in the range of 135° to 180°. The two graphs in FIGS. 2 and 3 show the close correlation between the mathematical model for determining scattered light intensity and actual measurements of scattered light intensity. The line in FIGS. 2 and 3 represents the intensity of light scattered off 20 μm diameter spherical drops illuminated with a 650 nm light beam at a distance of 30 mm from the drops as determined by analytical solution of the Mie equation for spherical particles. The circles in FIGS. 2 and 3 represent actual measurements of the intensity of light scattered off water drops nominally 20 μm in diameter fired from an inkjet printhead and illuminated with a VCSEL (vertical cavity surface emitting laser) emitting an 850 nm light beam. Scattered light intensity was measured with a PIN diode detector located 30 mm from the drops.

Referring to FIG. 2, the illuminating laser beam with an average power density of about 100 mW/cm$^2$ produces an intensity of scattered light that varies from more than 100-1000 nW/cm$^2$ at lower scatter angles θ to 1-10 nW/cm$^2$ at higher scatter angles θ. Although the scattered light is most intense at very low scatter angles ("front" scattering), the scattered light may be sufficiently intense at higher angles, through both "side" scattering and "back" scattering zones, to detect and characterize the drops. Referring now also to the detail view of FIG. 3, the intensity of scattered light increases significantly as the scatter angle θ approaches 180° for water droplets and for many water based solutions including inks. A comparatively high magnitude scatter signal may be generated by detecting scattered light within a tight scatter cone 16 (FIG. 1) near complete back scatter, i.e., at scatter angles very close to 180°. Thus, drop detection may be performed within a narrow range of scatter angles close to 180°. Current modeling indicates the scattered light intensity is approximately four times greater for a scatter cone $178° \leq \theta \leq 180°$ than for θ<178°. It is expected that the advantages of near complete back scatter drop detection may be achieved for scatter angles between about 177° and 180° (177°≦θ180°).

Complete back scatter and near complete back scatter drop detection helps make the drop detector less sensitive to operating distances within inkjet printers and other drop dispensing devices, and helps simply the installation and integration of light scattering drop detectors into such devices. For example, the drop detector may be assembled into a single module, allowing much of the alignment between the light source, light detector and any detector optics to be done during fabrication of the drop detector. A laser diode or other light source with a line profile covering the drop zone and the light detector may share the same lens for beam shaping and light collecting purposes. A complete or near complete back scattering configuration also allows a stationary light source/detector module used with a scanning reflector to increase the spatial coverage of the drop detector, reducing the need for a movable light source/detector module.

FIGS. 4-6 illustrates various embodiments of a drop detector 22 that utilizes complete and near complete back scattering such as a light scatter cone 16 shown in FIG. 1. Referring first to FIG. 4, drop detector 22 includes a light source 24, a light detector 26 and optics 28. Light source 24 projects a beam of light 12 to illuminate drop 10. Light detector 26 detects light 14 scattered off illuminated drop 10. Optics 28 direct and/or shape light beam 12 and/or scattered light 14. In the embodiment shown in FIG. 4, optics 28 includes a beam splitter 30 that is substantially transparent to light beam 12 but redirects scattered light 14 toward light detector 26 which, in this embodiment, faces light beam 12. Scattered light 14 in FIG. 4 represents generally rays of light completely back scattered (θ=180°) or a light cone of complete and near complete back scattered light (177°≦θ≦180°). Light source 24 and light detector 26 cannot occupy the same physical space. Thus, beam splitter 30 allows a light detector 26 offset from light source to detect complete and near complete back scattered light 14.

In the embodiment shown in FIG. 5, optics 28 includes a lens 31 for focusing light beam 12 and a lens 32 for collecting scattered light 14 for light detector 26 which, in this embodiment, faces along beam 12 next to light source 24. Although other configurations are possible, a focusing lens 31 for the outgoing light beam 12 and a collecting lens 32 for the incoming scattered light 14 may be desirable in implementations where the focal length of the optical path between light source 24 and drop 10 is different from the focal length of the optical path between drop 10 and light detector 26. Collecting lens 32, for example, may be a bifocal lens, a lens that is hollow in the center, a fraction of a spheric lens, or an aspheric lens. In the embodiment shown in FIG. 6, optics 28 includes a beam splitter 30, a lens 32 and a rotating mirror or other suitable reflector 34. Light source 24 projects light beam 12 on to a rotating polygon or scanning MEMS (micro-electromechanical system) mirror (e.g., a galvo scanner) 34, for example, to scan light beam 12 along drops 10. Scattered light 14 reflects back off the rotating mirror 34 to light detector 26 through collecting lens 32 and beam splitter 30.

Light source 24 represents generally any source of a light beam 12 suitable for illuminating drops 10 including, for example, EELs (edge emitting lasers), VCSELs (vertical cavity surface emitting lasers) and LEDs (light emitting diodes). Light detector 26 represents generally any light detector suitable for detecting light scattered off drops 10 including, for example, PIN detectors with integrated transimpedance amplifier, or discrete PIN detectors with external transimpedance amplifier, avalanche photodetector and phototransistors.

Figure 7:
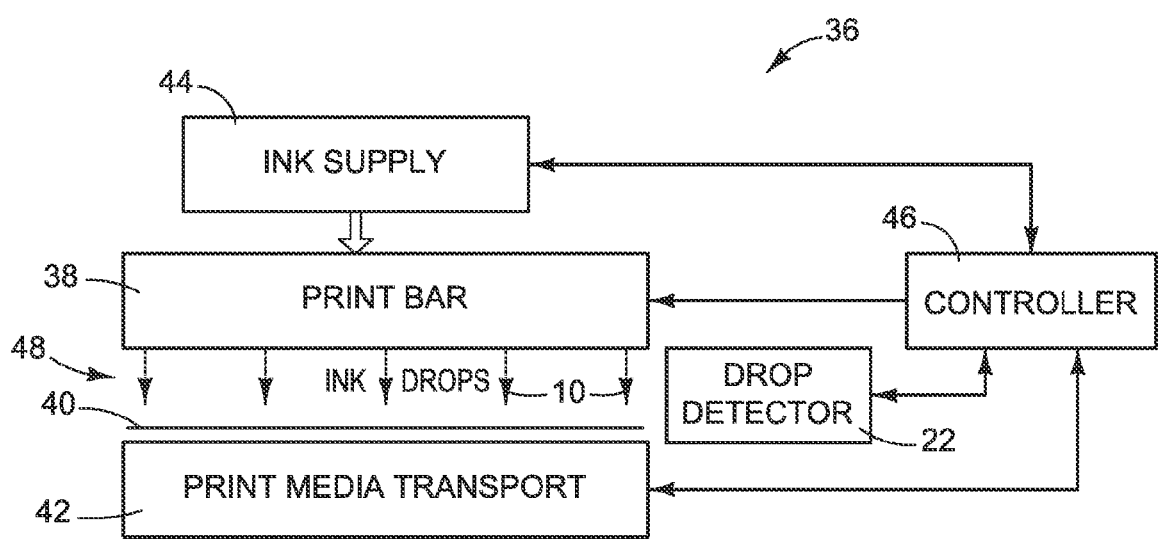
FIG. 7 is a block diagram illustrating one embodiment of an inkjet printer.

FIG. 7 is a block diagram illustrating one embodiment of an inkjet printer 36 that includes a print bar 38 spanning the width of a print media 40. Printer 36 also includes a media transport mechanism 42, a drop detector 22, an ink supply 44, and an electronic printer controller 46. Controller 46 represents generally the programming, processor(s) and associated memories, and the electronic circuitry and components needed to control the operative elements of a printer 36. Print bar 38 represents generally an array of printhead modules each carrying one or more printhead dies and the associated mechanical and electrical components for dispensing ink drops on to a sheet or web of paper or other print media 40. Print bar 38 may be a single print bar spanning media 40 or multiple print bars that together span media 40. For convenience, print bar 38 is referred to in the singular in the remainder of this Description. A typical thermal inkjet printhead die, for example, includes an orifice plate arrayed with ink ejection orifices and firing resistors formed on an integrated circuit chip positioned behind the ink ejection orifices. The printhead die(s) in each module are electrically connected to printer controller 46 and fluidically connected to ink supply 44. In operation, printer controller 46 selectively energizes ink ejector elements in a printhead die, or group of printhead dies, in the appropriate sequence to eject ink on to media 40 in a pattern corresponding to the desired printed image.

Figure 10:
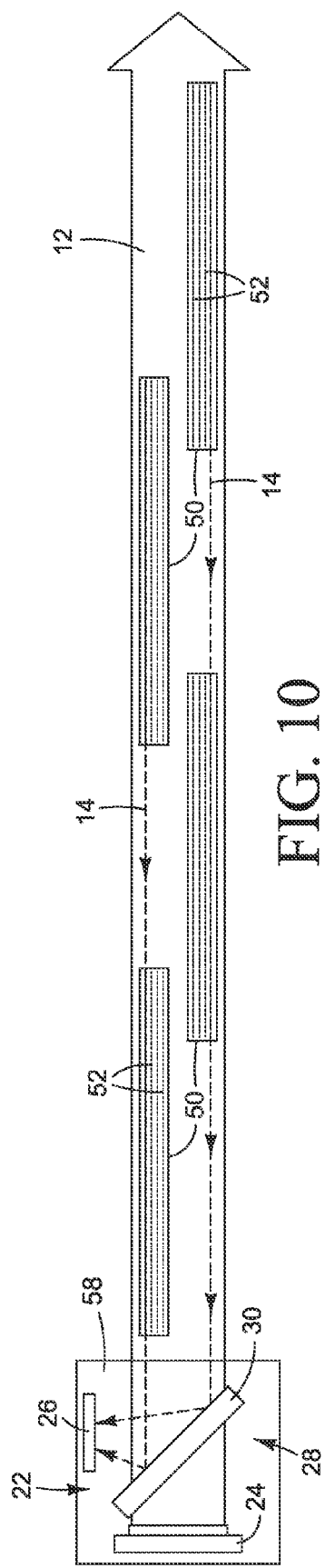
FIGS. 10 and 11 are plan and side elevation views, respectively, illustrating one embodiment of a stationary drop detector such as might be used in the printer shown in FIG. 7.
Figure 11:
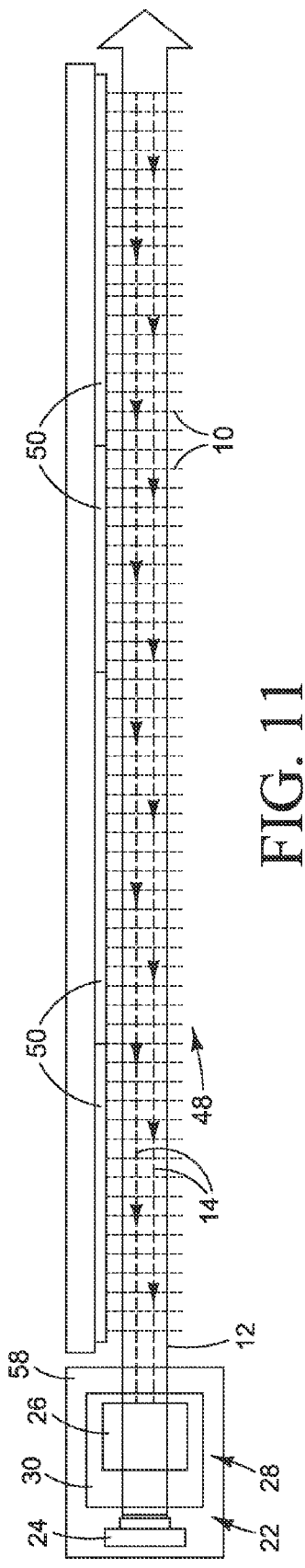

FIGS. 8 and 9 are plan and end elevation views, respectively, illustrating one embodiment of a carriage mounted, movable drop detector 22 such as might be used in printer 10 shown in FIG. 7. (For clarity, the scale of FIG. 9 is expanded compared to FIG. 8.) FIGS. 10 and 11 are plan and side elevation views, respectively, illustrating one embodiment of a stationary drop detector 22 such as might be used in printer 10 shown in FIG. 7.

Referring first to FIGS. 8 and 9, print bar 38 includes a media wide array of four stationary printhead modules 50. Each module 50 includes one or more printhead dies for ejecting ink drops through drop zone 48. (Individual printhead dies are not depicted in FIGS. 8 and 9.) Ink drops 10 are ejected from the printhead die(s) on each module 50 through an array of ink ejection orifices 52. Each orifice array 52, for example, may be used to eject a different color ink. Drop detector light source 24, light detector 26 and optics 28 are carried together on a carriage 54. (Light detector 26, which would appear behind beam splitter 30 in the end elevation view of FIG. 9, is omitted from FIG. 9 for clarity.) Carriage 54 moves laterally on a guide rail 56 back and forth along drop zone 48 in a direction transverse to the direction media 40 moves past print bar 38 (media transport direction) and transverse to the direction drops 10 move through drop zone 48 (drop direction). In some embodiments for a printer 36 (FIG. 7) these three directions will be substantially orthogonal to one another. Other configurations are possible and embodiments are not limited to orthogonal directions of movement. Thus, a transverse direction for carriage 54 is across but not necessarily perpendicular to the media transport direction or to the drop direction.

With continued reference to FIGS. 8 and 9, light source 24 projects a light beam 12 through focusing lens 31 to drop zone 48 at desired locations along drop zone 48, for example at the direction of controller 46 (FIG. 7). Light 14 back scattered off drops 10 is directed to light detector 26 by optics beam splitter 30. Light detector 26 outputs an electrical signal representative of scattered light 14. The signal may be analyzed, for example by controller 46 in FIG. 7, to determine characteristics of drops 10. Back scattering drop detection enables a carriage mounted drop detector 22 that is completely outside drop zone 48. As shown in FIGS. 8 and 9, for example, there is no part of drop detector 22 or carriage 54 that blocks any part of drop zone 48. By contrast, in a conventional carriage mounted ODD (optical drop detector) in which the light source and light detector must be located on opposite sides of the drop zone (scatter angle θ=0°), part of the carriage and/or drop detector necessarily blocks part of the drop zone.

A new carriage mounted back scattering drop detector 22 such as that shown in FIGS. 8 and 9 may be used to scan drop zone 48 without blocking any ink drops 10. Close alignment of the light source, drops and light detector is required for conventional ODD. Thus, a stepper motor is needed for a carriage mounted ODD to achieve the required alignment—a repeating sequence of moving the carriage, stopping the carriage, and then detecting drops. Close alignment is not critical for the new carriage mounted detector as the light beam crosses drop zone 48 and light scattered off drops 10 is detected by light detector 26. Drops 10 may be detected as carriage 54 scans light beam 12 along drop zone 48. Drop detection may be performed even during operations in which drops 10 are ejected simultaneously at locations outside the viewing area of detector 26. In addition, drop detector 22 and carriage 54 may be configured more compactly because there is no need to straddle drop zone 48, thus allowing more efficient movement of carriage 54.

In one embodiment, carriage 54 is moved to discrete locations along drop zone 48 where light source 24 is energized to project light beam 12 to detect drops 10 at each location. In another example, carriage 54 is scanned along drop zone 48 while light source 24 continuously projects light beam 12 to detect drops 10. A scale and encoder or other suitable position detector may be used to synchronize the movement of carriage 54 with the ejection of drops 10 and to correlate the relative positions of carriage 54 (and thus light source 24 and light detector 26) and ink drops 10 as light scattered off drops 10 is detected and the detection signals transmitted to controller 46 (FIG. 7). Scanning drop detection may be performed in multiple passes of a faster carriage scan back and forth along drop zone 48 or in one pass of a slower carriage scan along drop zone 48.

Referring now to FIGS. 10 and 11, print bar 38 includes a media wide array of four stationary printhead modules 50. Each module 50 includes one or more printhead dies (not shown) for ejecting ink drops through drop zone 48. Ink drops 10 are ejected from the printhead die(s) on each module 50 through an array of ink ejection orifices 52. The components of drop detector 22 (light source 24, light detector 26 and optics 28) are housed together in a single, stationary module 58 positioned at one end of drop zone 48. Light source 36 projects a light beam 12 along the length of drop zone 48. Light 14 back scattered off drops 10 is directed to light detector 26 by optics beam splitter 30. Light detector 26 outputs an electrical signal representative of scattered light 14. The signal may be analyzed, for example by controller 46 in FIG. 7, to determine characteristics of drops 10.

As noted at the beginning of this Description, the exemplary embodiments shown in the figures and described above illustrate but do not limit the invention. Other forms, details, and embodiments may be made and implemented. Therefore, the foregoing description should not be construed to limit the scope of the invention, which is defined in the following claims.

What is claimed is:

1. A drop detector, comprising:
   a light source for illuminating drops passing through a drop zone, the light source operable to emit a beam of light for illuminating drops passing through the drop zone; and
   a light detector positioned near the light source to detect light scattered off the drops back toward the light source at a scatter angle θ in the range of 177° to 180°, where θ represents a direction of scattered light measured with respect to an axis of the light beam with θ=0° lying along the axis in a direction of travel of the light beam and θ=180° lying along the axis opposite the direction of travel of the light beam.

2. The drop detector of claim 1, wherein the light detector is positioned near the light source to detect substantially only light scattered off the drops at a scatter angle θ in the range of 177° to 180°.

3. A drop detector, comprising:
   a light source operable to emit a beam of light for illuminating drops passing through a drop zone;
   a light detector near the light source for detecting light scattered off the drops back toward the light source; and
   a beam splitter positioned between the light source and the light detector, the beam splitter configured to be substantially transparent to the light beam and to direct the scattered light toward the light detector.

4. The drop detector of claim 3, further comprising a lens positioned between the light source and the drop zone for shaping the light beam and/or the scattered light.

5. The drop detector of claim 3, further comprising a rotating light reflector positioned between the light source and the drop zone for scanning the light beam along the drop zone.

6. The drop detector of claim 5, wherein the rotating light reflector comprises a scanning MEMS mirror.

7. The drop detector of claim 3, wherein the light source and the light detector are movable together on a carriage along one side of the drop zone in a scanning direction transverse to a drop direction.

8. The drop detector of claim 3, wherein the light source and the light detector are housed together in a stationary module at one end of the drop zone.

9. A drop detector, comprising:
   a light source operable to emit a beam of light for illuminating drops passing through a drop zone; and
   a light detector positioned near the light source to detect substantially only light scattered off the drops at a scatter angle θ in the range of 177° to 180°, where θ represents a direction of scattered light measured with respect to an axis of the light beam with θ=0° lying along the axis in a direction of travel of the light beam and θ=180° lying along the axis opposite the direction of travel of the light beam.

10. The drop detector of claim 9, wherein the light source and the light detector are movable together on a carriage along the drop zone in a scanning direction transverse to a drop direction.

11. The drop detector of claim 9, wherein the light source and the light detector are housed together in a stationary module near the drop zone.

12. A method for detecting drops passing through a drop zone, the method comprising:
   illuminating drops passing through the drop zone with a beam of light; and
   detecting light scattered off the drops back toward a source of the light beam at a scatter angle θ in the range of 177° to 180°, where θ represents a direction of scattered light measured with respect to an axis of the light beam with θ=0° lying along the axis in a direction of travel of the light beam and θ=180° lying along the axis opposite the direction of travel of the light beam.

13. The method of claim 12, wherein detecting light scattered off the drops at a scatter angle θ in the range of 177° to 180° comprises detecting substantially only the light scattered off the drops at a scatter angle $\theta$ in the range of 177° to 180°.

14. The method of claim 12, further comprising moving the beam of light along the drop zone to illuminate drops at different locations along the drop zone while detecting light scattered off the drops at a scatter angle $\theta$ in the range of 177° to 180°.

15. The method of claim 14, wherein moving the beam of light along the drop zone comprises scanning the beam of light along the drop zone.

16. The method of claim 15, wherein scanning the beam of light along the drop zone comprises projecting the beam of light on to a rotating light reflector.

17. The method of claim 15, wherein scanning the beam of light along the drop zone comprises scanning a source of the beam of light along the drop zone.

\* \* \* \* \*